United States Patent [19]

Mears

[11] Patent Number: 4,553,272
[45] Date of Patent: Nov. 19, 1985

[54] REGENERATION OF LIVING TISSUES BY GROWTH OF ISOLATED CELLS IN POROUS IMPLANT AND PRODUCT THEREOF

[75] Inventor: Dana C. Mears, Oakmont, Pa.

[73] Assignee: University of Pittsburgh, Pittsburgh, Pa.

[21] Appl. No.: 238,374

[22] Filed: Feb. 26, 1981

[51] Int. Cl.[4] .............................................. A61F 1/00
[52] U.S. Cl. .................................... 623/1; 128/92 C; 128/92 G; 623/10; 623/16
[58] Field of Search ........................ 128/92 G; 3/1.9, 1

[56] References Cited

U.S. PATENT DOCUMENTS

| | | | |
|---|---|---|---|
| 2,621,145 | 12/1952 | Sano | 167/84 |
| 3,514,791 | 6/1970 | Sparks | 3/1 |
| 3,849,805 | 11/1974 | Leake et al. | 3/1 |
| 3,905,047 | 9/1975 | Long | 3/1.9 |
| 3,905,777 | 9/1975 | Lacroix | 29/183.5 |
| 3,971,134 | 7/1976 | Bokros | 3/1 |
| 3,992,725 | 11/1976 | Homsy | 3/1 |
| 4,000,525 | 1/1977 | Klawitter et al. | 3/1.911 |
| 4,005,495 | 2/1977 | Locke et al. | 3/1.91 |
| 4,051,598 | 10/1977 | Sneer | 128/92 C X |
| 4,070,514 | 1/1978 | Eatherly et al. | 3/1.9 X |
| 4,073,999 | 2/1978 | Bryan et al. | 3/1.9 X |
| 4,255,820 | 3/1981 | Rothermel et al. | 3/1 |
| 4,330,891 | 5/1982 | Branemark et al. | 128/92 C X |

FOREIGN PATENT DOCUMENTS 2412300  7/1979  France ..................... 128/92 G

Primary Examiner—Richard J. Apley
Assistant Examiner—David Isabella
Attorney, Agent, or Firm—Arnold B. Silverman

[57] ABSTRACT

A method of repair of patient tissues by implant including providing a living cell sample which is introduced into an implant member having a porous open structure. The cell sample may be cultured in the implant. The implant is secured to the patient, as by surgical implantation. In one embodiment, the implant portion which receives the cells preferably has a pore size of about 25 to 75 microns. In addition, a second pore size of about 100 to 400 microns for receipt of blood vessels and osteogenus cells through ingrowth after introduction into the patient, may be provided. The cell sample may advantageously be selected from the group consisting of cartilage cells, tendon cells, ligament cells and musculotendinous cells. The implant member may be advantageously used in bone or joint reconstruction surgery and in other forms such as artificial tooth implantation.

A surgical implant comprising an inert member having, in one embodiment, a first series of open pores of an average size of about 25 to 75 microns and a second series of open pores of an average size of about 100 to 400 microns with patient cells growing within the pores.

2 Claims, 6 Drawing Figures

REGENERATION OF LIVING TISSUES BY GROWTH OF ISOLATED CELLS IN POROUS IMPLANT AND PRODUCT THEREOF

BACKGROUND OF THE INVENTION

1. Field of the Invention

This invention relates to the regeneration of living tissues by ingrowth of isolated patient cells into porous implants and the method of using the same in surgical procedures.

2. Description of the Prior Art

Numerous means of attempting to reconstruct human and animal bones and joints which have been damaged through injury or disease such as arthritis, for example, have been known.

It has been known to surgically remove a damaged or diseased joint and replace it with an artificial joint. Among the problems encountered with such procedures are the fact that the joint which is artificial does not possess the natural joint's ability to undergo continuous repair in order to replace effete matrix material and the further fact that it lacks the defense mechanisms against infection. Further, such joints tend to generate toxic wear particles of materials such as metal or plastic.

It has also been known to use transplantation of cadaveric or animal joints. These attempts have generally been unsuccessful as a result of inadequate revascularization of the implanted joints and immunologic rejection of the allografts or zenografts.

U.S. Pat. No. 4,005,495 discloses a ceramic cap bone prosthesis and a method of implantation of the same. U.S. Pat. No. 4,000,525 discloses a ceramic prosthesis said to be suitable for the tibial plateau of a knee joint.

U.S. Pat. No. 2,621,145 discloses a flexible strip of particles of bone held together by a fibrin network positioned on a carrier strip of a material such as cellophane. This is said to encourage rapid regrowth of bone by the body. The material, however, does not have the mechanical strength to permit replacement of a structural portion of the body therewith. It also lacks an isoelastic substrate for effective restitution of biological matrix.

U.S. Pat. No. 3,992,725 describes a method for ingrowth of bone which is positioned immediately adjacent the porous substrate. This disclosure is limited to use in connection with bone tissue which is located immediately adjacent to the porous substrate and discloses a material which would appear to be unsuitable for other tissues of lower modulus of elasticity.

Lacroix, U.S. Pat. No. 3,905,777 discloses invasion of adjacent bone into a porous substrate. The principle thrust of this disclosure is directed toward providing a superficial coating on an otherwise conventional implant.

U.S. Pat. No. 3,849,805 discloses a nonmetallic mesh, bone induction tray which has a plurality of pores and is adapted to contain bone chips. This disclosure also relates to passive ingrowth of bone into an adjacent implant. It does not permit reconstitution of tissue different from an adjacent one. Also, regeneration of bone from chips is undesirable as the bone may form alternatively either fibrous tissue or cartilage or a combination of fibrous tissue, cartilage and bone.

Long U.S. Pat. No. 3,905,047 discloses a bone prosthesis which consists of a ceramic body having a matrix within which a number of discrete particles of a refractory oxide are imbedded and bonded together. The biodegradable nature of the structure can produce potentially toxic degradation products. Also, the high modulus of elasticity makes it vulnerable to undergo brittle fracture.

There remains, therefore, a very real and substantial need for a method of permitting reconstruction of musculoskeletal tissues regardless of whether they are originally present in the region of the implant and in such fashion as to provide resistance to infection, mechanical strength and avoidance of the above-described problems. There is a further need for a product which will effectively accomplish these obejctives.

SUMMARY OF THE PRESENT INVENTION

The above-described need has been met by the present invention. The present invention contemplates a method wherein isolated daughter cells are introduced into a porous implant member and cultured therein. The implant member is secured to the patient so as to permit continued cell growth resulting in reconstruction of the desires tissue. In one embodiment, the pore size of at least a portion of the implant member is preferably an average of about 25 to 75 microns. In addition, it is contemplated that for some reconstruction it may be desirable to provide a larger size pore on the order of about 100 to 400 microns, for example, to permit ingrowth of blood vessels in osteogenus cells after surgical implant has been completed. A barrier between the two pore sizes may advantageously be provided. The method may be employed in connection with cartilage cells, tendon cells, bone cells, ligament cells, organ cells, teeth and musculotendinous cells, for example.

The product consists of the open-pored implant containing the isolated daughter cells. The implant is shaped to the desired configuration for joint reconstruction or reconstruction of a portion of a joint, bone or such other use as desired. The implant may take the form of a maxilla facial part of an artificial tooth.

It is an object of the present invention to provide a method and system for regeneration of living tissues by ingrowth of isolated daughter cells into porous, inert implant members.

It is a further object of this invention to provide such a system wherein reconstruction of the desired tissues is independent of the presence of such cells adjacent to the point of surgical implanting.

It is another object of this invention to provide such a system which permits the reconstructed joint or other body part to exhibit natural tendencies toward resistance to infection.

It is another object of this invention to provide such a system which avoids the undesired, potentially toxic wear particles resulting from bearing surface contact in the artificial joints.

It is another object of this invention to provide such a systtem which is particularly advantageously used in connection with reconstruction of cartilage tissue, tendon tissue, ligament tissue, bone, teeth and musculotendinous tissue.

It is a further object of the present invention to provide such a system which establishes the desired mechanical strength and elasticity closely approximating that of the portion of the body which is being reconstructed or repaired.

It is a further object of this invention to provide such implants which may be surgically secured to the patient by conventional surgical techniques.

It is yet another object of this invention to provide such a system which is economical to employ.

These and other objects of the invention will be more fully understood from the following description of the invention on reference to the illustrations appended hereto.

DESCRIPTION OF THE PREFERRED EMBODIMENTS

Figure 1:
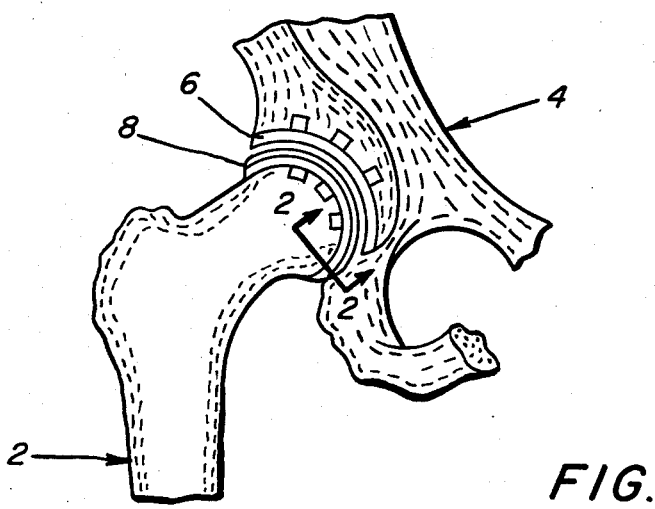
FIG. 1 illustrates a partially schematic arthritic joint which has been treated by the process of the present invention.

As used herein, the term "patient" shall include both human beings and animals. It will be appreciated that the present invention will have substantial use in veterinary medicine as well as in treating humans.

The present invention provides a method for regenerating structural and supportive tissues of a patient's body. Among the tissues which may be regenerated in this fashion are cartilage tissue, tendon tissue, ligament tissue, organ tissue, bone tissue, teeth and musculotendinous tissues, for example.

In general, the procedure involves removing daughter cell samples from other healthy joints or other appropriate tissues within the patient. The daughter cells are cultured and placed in an inert, porous implant. Alternatively if the yield of daughter cells from the patient is sufficiently great, the cells may be placed directly into the implant with or without subsequent culturing prior to or after implantation within the patient, the tissue continues to grow so as to provide the desired reconstruction.

The implant has a porous, open structure for receipt of the autologous daughter cells and growth therein. The implant may advantageously be made from a material selected from the group consisting of titanium and its alloys, surgical-quality stainless steel alloys, fiber reinforced composite materials, graphite composite materials, (such as graphite-graphite or graphite-polymer composites), quartz, graphite, polyethylene and other polymers and colbalt-chromium alloys.

The implant pores which receive the daughter cells and contain the tissue grown therewithin during culturing and thereafter, preferably have a pore size on the order of 25 to 75 microns with 50 to 70 microns being the preferred range. On a volume basis, it is preferred that the pore openings be about 20 to 50 percent of the of the total implant volume with about 30 to 40 percent being the preferred volume relationship. It is generally desirable to effect a balance between desired strength and porosity. For some uses where the site of attachment is adjacent to bone, the implant may be provided with another series of pores which are larger and may be about 100 to 400 microns in size. These larger pores serve to permit ingrowth of blood vessels and adjacent osteogenic cells after implantation in the patient. Where both pore sizes are provided, it is preferred to establish a barrier between the two pore sizes so as to resist undesired commingling of the tissue generated by the daughter cells with the blood vessels and osteogenic cells which are ingrown in the patient.

Among the preferred means of securing implants are one or more of the following: mechanical wedge fit, mechanical fasteners and grouting. In the mechanical wedge fit approach, outwardly projecting pegs formed in the implant are force fit into corresponding openings of slightly smaller size in the adjacent bone. Such pegs will vary in dimension depending upon the implant size, bone size and implant location. A peg for a hip joint might, for example, be of cylindrical shape and have a length of about $\frac{1}{2}$ inch and a diameter of about 75 to 125 mm, with the peg-receiving opening in the bone being of slightly smaller diameter. Pores will generally be provided to permit desired ingrowth.

If desired, screws or other mechanical fasteners may be employed to secure an implant to a bone.

In employing grouting, the grouting material is introduced into pores of the implant and openings in the bone to effect securement. In using this approach, only a portion of the implant pores should be filled with grouting as voids for desired ingrowth should be maintained.

Figure 2:
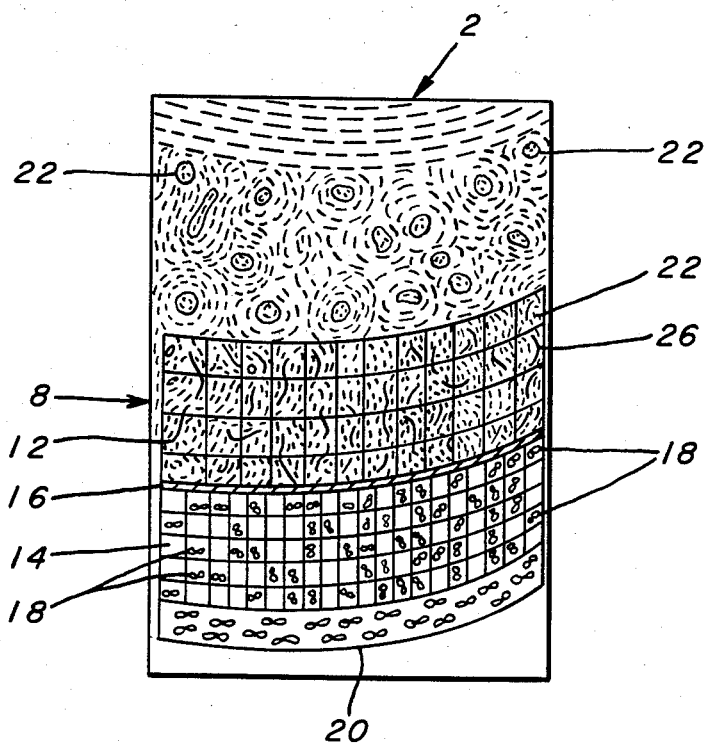
FIG. 2 is an exploded fragmentary cross sectional view of a portion of the joint shown in FIG. 1 taken generally along 2—2.

Referring now in greater detail to FIG. 1 and 2, there is shown an arthritic hip joint which has been surgically reconstructed by the method and product of the present invention. As is shown in FIG. 1, the femur 2 and hip bone 4 are provided with porous implants 6, 8 of the present invention which serve to re-establish the ball and socket hip joint. As is shown in FIG. 2, which illustrates a section through porous implant 8 and the related femur 2, the porous implant has a series of first pores 12 which may have an average pore diameter of about 100 to 400 microns and preferably have an average pore size of about 150 to 250 microns. The adjacent portion of the implant 8 is provided with a series of pores 14 which may have an average pore opening of about 25 to 75 microns and preferably have an opening of about 50 to 70 microns. In order to minimize communication between the first series of pores 12 and the second series of pores 14, it is preferred to provide an intermediate barrier member 16 which is preferably integrally formed within the porous implant 8.

An example of how the present invention may be employed in the context of the embodiments illustrated in FIGS. 1 and 2 will now be considered. Daughter cells 18 taken from the same patient from a region other than the hip joint which is to receive the surgical implants are introduced into the second series of pores 14 of implant 8. The daughter cells may be living articular chondrocytes. The cells are isolated from the surrounding matrix such as articular cartilage. Culturing may be advantageously effected in the presence of a suitable nutrient media at about 36° to 38° C. for about one to two weeks. The implant 8 either prior to introduction of the daughter cells or thereafter may be trimmed to conform to the desired shape required for the particular reconstructive surgery. The implant 8 is then surgically inserted and secured to the upper end of the femur 2 as by one or more of the methods disclosed above.

As is shown in FIGS. 1 and 2, after a suitable period of continued growth within the patient such as approximately 20 to 30 days, it is noted that a layer 20 of articular cartilage tissue has been generated as the result of growth of cells 18 within pores 14 and therebeyond. This serves to provide a natural tissue bearing surface for the reconstructed ball and joint socket. It is noted that osteogenic cells have grown into the large pores 12 of porous implant 8 to thereby improve the mechanical integrity of the reconstructed joint. It is also noted that blood vessels 26 have experienced ingrowth into the large pores 12. This serves to facilitate desired blood supply to this region. Similar reconstructive action occurs as a result of porous implant 8 disposed on the hip bone 4. It will be appreciated that in this fashion although the region of the implant may have been totally devoid of cartilage cells, reconstruction of natural cartilage tissue in this area and effective mechanical integrity of joint are provided. In addition, as there are no artificial materials to provide potentially toxic waste products, this problem encountered with artificial replants is avoided. In addition, as a result of the creation of natural tissues through regrowth, the joint possesses resistance to infection and will tend to have a lower coefficient of friction than artificial joints.

Figure 3:
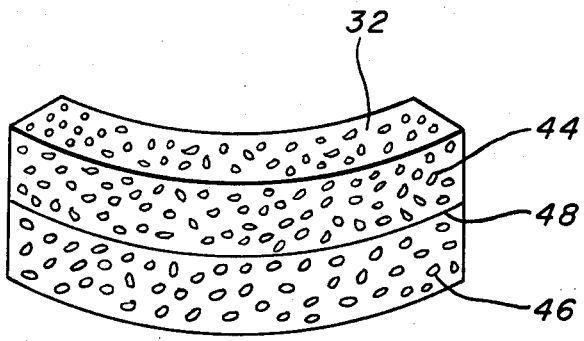
FIG. 3 is a perspective view of a form of implant of the present invention.
Figure 4:
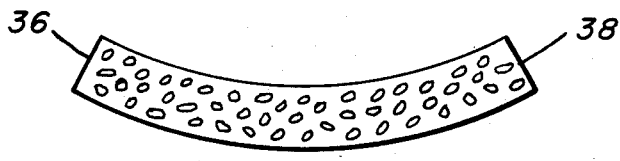
FIG. 4 is a top-plan view of the implant shown in FIG. 3.
Figure 5:
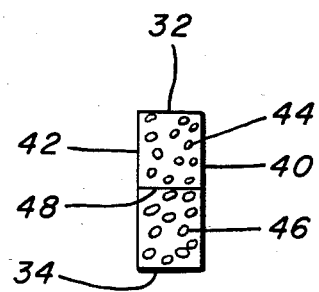
FIG. 5 is a right-side elevational view of the implant shown in FIG. 3.

Referring now to FIGS. 3 through 5, there is shown a schematic detail of a form of implant which may be used advantageously for implants 8 in FIGS. 1 and 2. It will be appreciated, however, that a wide variety of other shapes and sizes may be required depending upon the end use application. As is shown in these figures, the implant is of generally curved shape with a substantially rectangular cross-sectional configuration. In the form shown, the upper surface 32 is generally parallel to lower surface 34 and substantially perpendicular to faces 40, 42. A pair of substantially rectangular end walls 36, 38 are provided. It will be appreciated that the inert implant member has an open pore structure. In the form shown, the upper pores 44 may be of a substantially different size from the lower pores 46 and a barrier 48 which serves to resist communication therebetween may be provided. If desired, the barrier may be provided in the form of a separate member which is molded or otherwise secured within the porous implant.

While the inert implant member may be made from a wide variety of materials which possess adequate porosity for cell retention and tissue growth as well as the desired mechanical characteristics, among the preferred materials are at least one material selected from the group consisting of titanium and its alloys, surgical quality stainless steel alloys, fiber reinforced composite materials, graphite composite materials, quartz, graphite, polyethylene and other polymers and cobalt-chromium alloys. It is also preferred that the implant member have a modulus of elasticity substantially equal to that of the bone or other member with which it will be associated or to which it will be secured.

Figure 6:
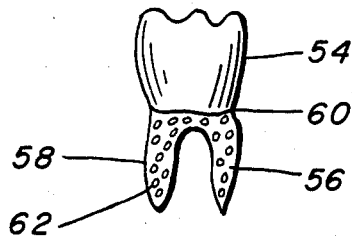
FIG. 6 is an elevational view of a form of tooth implant of the present invention.

Referring now to FIG. 6 there is shown a porous implant in the form of an artificial tooth. The tooth has a crown 54, roots 56, 58 and an interposed neck portion 60. It is noted that pores 62 are provided solely on the root portion. This permits the daughter cells to be introduced into the root and cultured. Subsequently the cells generate tissue below the gum line after the artificial tooth has been implanted into the patient. This serves to restore a natural type of retention for the artificial tooth. Also, it provides advantageous natural resistance to infection. If desired, the implant may take the form of a generally cylindrical post or peg which may be implanted and have an upwardly projecting portion to which an artificial tooth may be secured as by a suitable adhesive, for example.

In order to provide greater understanding of the invention, examples will be considered.

EXAMPLE 1

This example illustrates use of the invention in the cultivation of articular chondrocytes in vitro. Specimens of articular cartilage are harvested from the periphery of a normal joint from those sites that do not compromise the functional attributes of the joint in question. The fragments of articular cartilage are morsalized and subjected to enzymatic degradation with a balanced physiological solution containing 0.2% trypsin and 0.2% collagenase. The cells are separated from the matrix and collected with centrifugation or filtration. The cells are cultivated on the bottom of a flask in a suitable nutrient mixture such as F12 solution with supplements of 10% fetal calf serum and 1% penicillin. During a 10 day period about 1,000 clones develop in each culture dish/ At the end of the ten day period when the cells are forming clones, the culture medium is altered to CML medium 1066 with supplements of 10% fetal calf serum and 1% penicillen. This secondary cultivation is undertaken for approximately five days. If desired, the cells may be labeled with tritiated thymidine. At the end of the fifteen day period the cells are resuspended in a small quantity of a balanced physiological solution such as Geys medium. The rich cell suspension is infused into the sterile porous implants immediately after the surgical implantation of the implant.

EXAMPLE II

This example illustrates the use of the invention in the cultivation of periodontal ligament cell suspensions. To harvest the autologous periodontal ligamentous cells, the gingiva associated with the relevant donor tooth is incised. The root of the tooth is exposed and when necessary the tooth may be excised. The periodontal ligament is detached from the root and, when necessary, from the extracted root. Washings from the root are collected. The suspension medium consists of phosphate-buffered saline solution. By means of a scraping technique the periodontal ligament is removed from the root. Care is taken to avoid contamination with gingival cells. Also, the apical portion of the root is not employed to avoid possible contamination by cells associated with the underlying permanent tooth germ. The freed ligament is placed in a sterile glass tube containing the phosphate-buffered saline prior to centrifugation. The cell suspension is rewashed on three occasions. The cells are cultivated in a balanced physiological solution containing 15% fetal calf serum and penicillin 100 micrograms per ml. The cultures are incubated at 37 degrees C. in a humidified atmosphere of air +5 percent $CO_2$. The osmolarity of the medium is maintained between 310-317 mOsm. Ultimately the cells are resuspended in the physiological saline solution and the suspension is passed through a capillary glass-array filter of pore size 35-40 micro molar to obtain a single-cell suspension. Alternatively, the cell suspension is washed in a physiological solution +15 percent fetal calf serum and centrifuged at 1000 rpm prior to filtration. Subsequently, the cell suspension is prepared as an infusion for colonization in the sites of anchorage in the artificial teeth.

The implant of the present invention may be provided in the desired size and shape through direct manufacture of the ultimate product or manufacture of an oversized product which subsequently can be trimmed to the desired size and shape.

It is preferred that the material of the implant member generally possess isoelasticity with the biological tissue to be created through the cells While emphasis herein has been placed on the use of substantially rigid materials in creating the implant, it will be appreciated that for certain uses resilient, sponge-like materials or porous materials or synthetic cloth may be employed as the implant.

It will, therefore, be appreciated that the present invention provides a method and product for effecting reconstruction of joints, bones, ligaments, tendons, cartilage, muscles, musculofacial regions as well as artificial tooth implants. All of this is accomplished in a natural fashion which provides compatible mechanical properties for the implant and the surrounding body portions, eliminates the need to introduce potentially toxic materials which would have artificial wear particles, promotes growth of natural tissue to resist infection and restore the body to a more natural condition. This is accomplished with a simple and effective technique using generally standard culturing procedures and surgical techniques.

It will be appreciated that depending upon the particular use of the implant and process and the amount of cells obtained for implant from the host natural matrix, the initial culturing of the cells in a suitable nutrient media may be effected in the implant or in a separate location. Also, the cells if present in sufficient quantity either through prior culturing or the availability of a sizable portion from the host may be introduced into the matrix immediately prior to or after surgical implantation. In general, cultured cells replicate rapidly to produce a large number of cells within about ten to fifteen days. In general, post operative ingrowth with respect to bones and joints takes about twenty to forty days, but total restraint of the implant is not always necessary as some motion can contribute to fostering cell ingrowth.

While reference has been been herein to obtaining daughter cells from the patient receiving the implant, it will be appreciated that another donor may be employed with such precautions as may be necessary or desirable to avoid rejection being taken.

While for purposes of convenience of reference herein specific reference has been made to articular joints such as a hip joint, bone reconstruction and artificial tooth implants, it will be appreciated that the uses of the present method and product are not so limited and a wide variety of additional uses in addition to those examples specifically set forth herein will be apparent to those skilled in the art.

Whereas particular embodiments of the invention have been described above for purposes of illustration, it will be evident to those skilled in the art that numerous variations of the details may be made without departing from the invention as defined in the appended claims.

I claim:

1. A method of repair of patient tissues by implant comprising providing a starter cell sample, providing an implant member having a porous structure, providing said implant material with an open pore structure having a number of pores of an average pore size of about 25 to 75 microns, introducing said cell sample into the pores of said implant member, surgically effecting securement of said implant to said patient, whereby said cell sample will initiate growth within said pores and effect reconstruction of said tissues, providing said implant member with at least two distinct pore sizes, providing a first said pore size of about 100 to 400 microns and a second said pore size of about 25 to 75 microns, culturing said starter cells in said second pores, and providing a barrier separating said first pores from said second pores.

2. A surgical implant comprising an inert member having at least one series of open pores, said pores being about twenty to fifty percent of the total volume of said implant member, said series of pores having an average size of about 25 to 75 microns, patient cells disposed within said pores, said inert implant having a second series of open pores having an opening size of about 100 to 400 microns, and barrier means separating said first series of pores from said second series of pores.

* * * * *

UNITED STATES PATENT AND TRADEMARK OFFICE
CERTIFICATE OF CORRECTION

PATENT NO. : 4,553,272

DATED : Nov. 19, 1985

INVENTOR(S) : Dana C. Mears

It is certified that error appears in the above-identified patent and that said Letters Patent is hereby corrected as shown below:

On the Title Page, at the top of column 2, the date of the French patent should be --8/1979--.

Column 2, line 12, "obejctives" should be --objectives--.

Column 2, line 21, "desires" should be --desired--.

Column 2, line 57, "systtem" should be --system--.

Column 4, line 28, "FIG." should be --FIGS.--.

Column 6, line 19, "dish/" should be --dish.--

Column 6, line 22, "penicillen" should be --penicillin--.

Column 7, line 5, a period (.) should be inserted after "cells".

Column 7, line 40, "has been been" should read --has been made--.

Signed and Sealed this

Eighteenth Day of February 1986

[SEAL]

Attest:

DONALD J. QUIGG

Attesting Officer

Commissioner of Patents and Trademarks